(12) United States Patent
Wenk et al.

(10) Patent No.: US 8,328,809 B2
(45) Date of Patent: Dec. 11, 2012

(54) BONE PLATE FIXATION SYSTEM

(75) Inventors: Klaus Wenk, Constance (DE); Amanda L. Neher, Claypool, IN (US); Kyle A. Bohnenkamper, Warsaw, IN (US); Simona Paganetto, Winterthur (CH)

(73) Assignee: Zimmer, Inc., Warsaw, IN (US)

(*) Notice: Subject to any disclaimer, the term of this patent is extended or adjusted under 35 U.S.C. 154(b) by 163 days.

(21) Appl. No.: 12/683,953

(22) Filed: Jan. 7, 2010

(65) Prior Publication Data

US 2011/0166573 A1 Jul. 7, 2011

(51) Int. Cl.
*A61B 17/56* (2006.01)
(52) U.S. Cl. ............................... 606/71; 606/70
(58) Field of Classification Search ......... 606/86 B, 606/86 R, 87, 96–98, 104, 280–299
See application file for complete search history.

(56) References Cited

U.S. PATENT DOCUMENTS

| 4,364,382 | A * | 12/1982 | Mennen ..................... 606/283 |
| 6,183,474 | B1 | 2/2001 | Bramlet et al. |
| D469,874 | S | 2/2003 | Bryant et al. |
| D469,875 | S | 2/2003 | Bryant et al. |
| D470,588 | S | 2/2003 | Bryant et al. |
| D480,141 | S | 9/2003 | Benirschke et al. |
| 6,706,046 | B2 * | 3/2004 | Orbay et al. .................. 606/62 |
| 7,229,445 | B2 | 6/2007 | Hayeck et al. |
| D638,942 | S | 5/2011 | Wenk et al. |
| D642,685 | S | 8/2011 | Wenk et al. |
| D655,010 | S | 2/2012 | Wenk et al. |
| 2005/0049594 | A1 | 3/2005 | Wack et al. |
| 2006/0095044 | A1 | 5/2006 | Grady, Jr. et al. |
| 2006/0173458 | A1 | 8/2006 | Forstein et al. |
| 2007/0173843 | A1 * | 7/2007 | Matityahu ..................... 606/69 |
| 2008/0183172 | A1 | 7/2008 | Fritzinger |
| 2009/0312760 | A1 | 12/2009 | Forstein et al. |

FOREIGN PATENT DOCUMENTS

| WO | WO2009042510 A2 | 4/2009 |
| WO | WO2011/083084 A1 | 7/2011 |

OTHER PUBLICATIONS

Product Brochure—Zimmer NCB Plating System, A locking plate system that expands a surgeon's options in trauma surgery, 97-2370-001-00 5 ML, 2006 Zimmer, Inc.
Surgical Technique—Zimmer NCB Distal Femoral Plating System, The right locking option for tough fractures.
The International Search Report published Jul. 14, 2011 in related International Application No. PCT/EP2011/000038.

* cited by examiner

*Primary Examiner* — Kevin T Truong
*Assistant Examiner* — Diana S Jones
(74) *Attorney, Agent, or Firm* — Schwegman, Lundberg & Woessner P.A.

(57) ABSTRACT

A universal jig is compatible with bone plates of varying size, in which different plate sizes having different hole configurations. For example, a longer bone plate may have a first hole pattern along a given length thereof, while various shorter bone plates may have differing hole patterns along respective corresponding lengths. The universal jig includes a combination of hole groupings to provide a jig hole for each hole in the differing hole patterns of the longer and shorter plates, so that the universal jig is useable with a variety of bone plates having disparate hole patterns. For any given bone plate length and hole configuration, a masking cover may provided to attach to the jig. The masking cover masks off unused jig holes, so that only those jig holes intended for use with a particular bone plate are left exposed.

7 Claims, 11 Drawing Sheets

FIG_1

BONE PLATE FIXATION SYSTEM

BACKGROUND

1. Technical Field

The present disclosure relates to the fixation of orthopaedic structures to bones. More particularly, the present disclosure relates to jigs used in conjunction with bone plates in minimally invasive surgery (MIS).

2. Brief Description of the Related Art

Bone plates are used in a variety of surgical procedures, such as to treat fractures of bones in the body. For example, an elongate bone plate with a plurality of fixation holes along its extent may be used to affix the bone plate to multiple bone fragments of a fractured bone. The bone plate bridges the gaps created between bone fragments, i.e., the fracture gaps, thereby providing support for the fractured bone and aiding in the healing process.

Insertion and affixation of a bone plate to a fractured bone may be accomplished with minimally invasive surgery ("MIS"). MIS methods of bone plate fixation can include making a small incision at or near an end of a fractured bone, so that only the end of the bone is exposed to the surgeon. A bone plate may then be inserted through the incision such that a bone contacting surface of the bone plate abuts the relevant bone fragments, with the length of the bone plate spanning at least a portion of the length of the fractured bone and bridging the fracture gap. Once the plate is properly positioned, the bone plate is affixed to the bone by passing fasteners through the skin, into fixation holes in the bone plate, and into the bone on both sides of the fracture gap. This MIS technique can include making stab incisions through the outer layer of skin to provide access for cannulas, which are inserted through the outer layer of skin to span the distance between the incisions and the bone plate fixation holes, so that each cannula corresponds to a respective hole position on the bone plate. A fastener may then be passed through each respective cannula to affix the bone plate to the bone.

An existing jig and method of use are shown in two brochures published by Zimmer, Inc, namely the "Zimmer® NCB® Plating System" brochure, copyright 2006, and the "NCB® Distal Femoral Plating System, Surgical Technique" brochure, copyright 2005, 2007 and 2008, the disclosures of which are hereby incorporated by reference herein in their entireties, and copies of which are filed in an Information Disclosure Statement on even date herewith. Similar surgical techniques are may also be used with the bone plate fixation system of the present disclosure.

Figure 1:
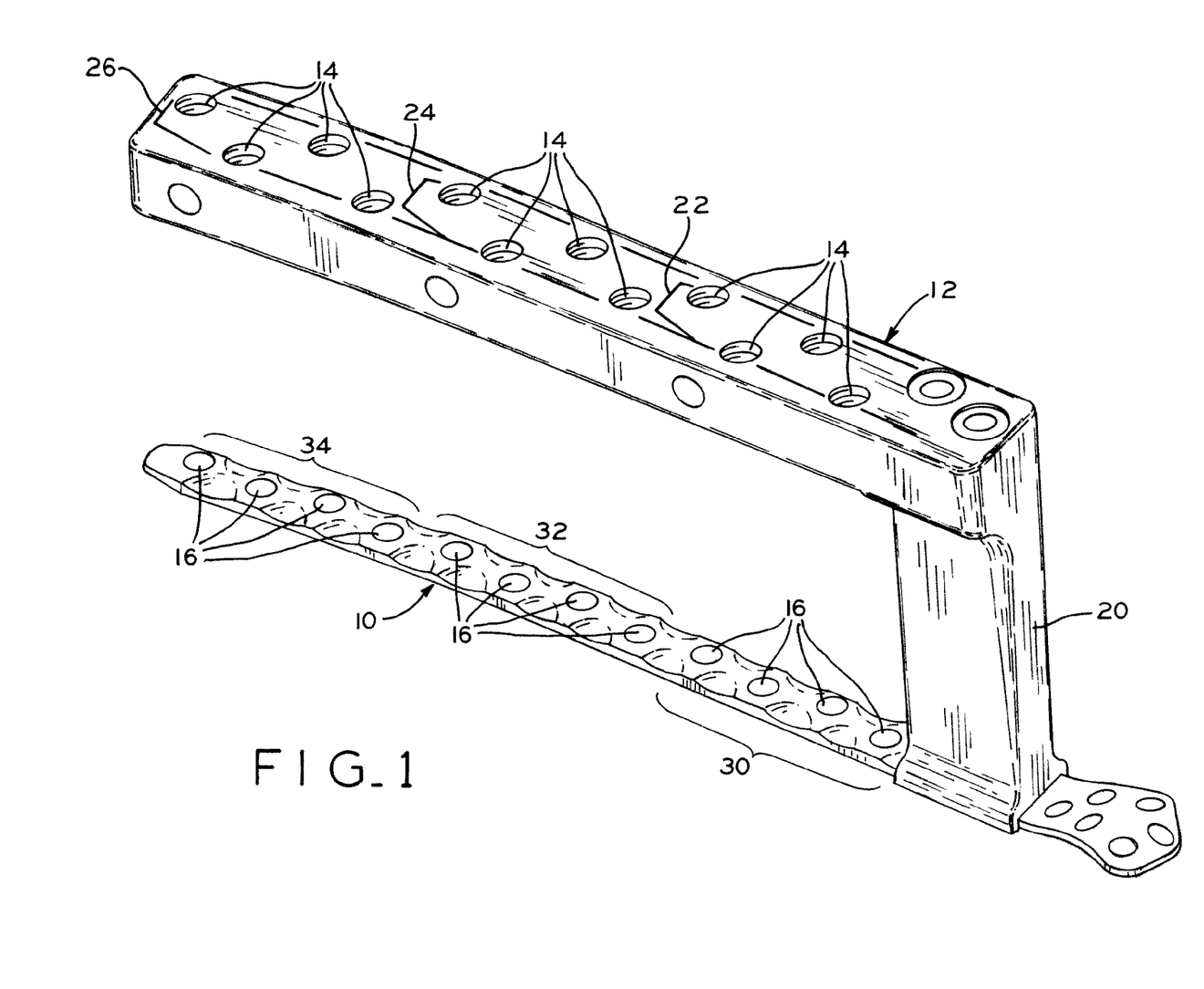
FIG. 1 is a perspective representation of a conventional jig attached to a bone plate.
Figure 2:
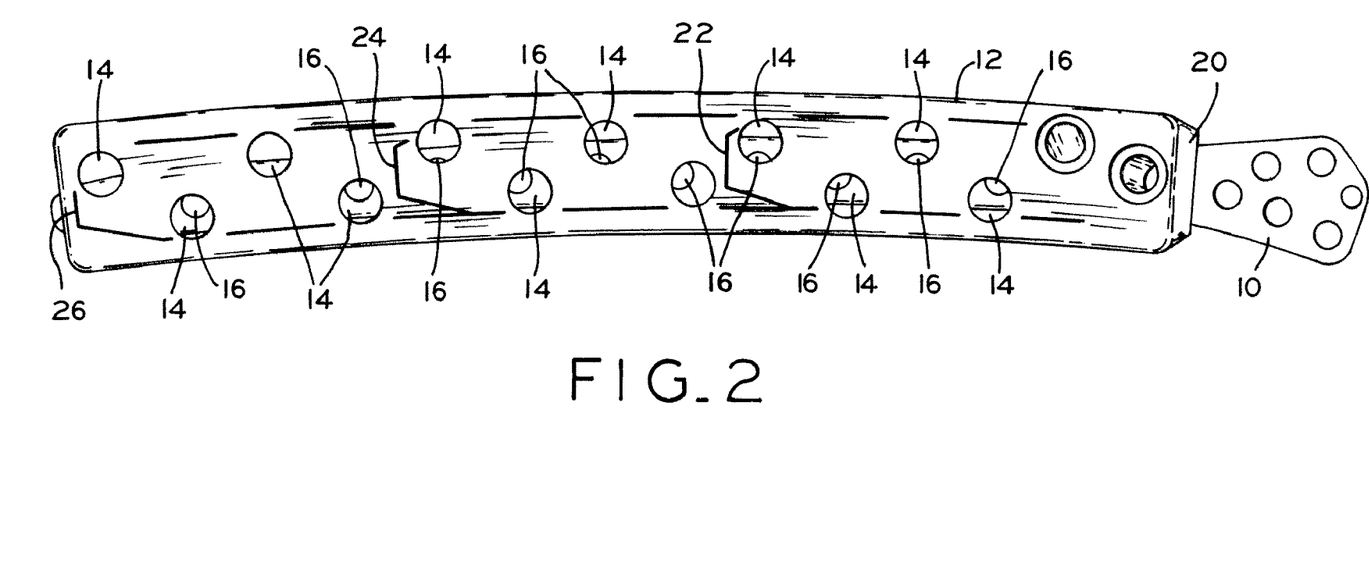
FIG. 2 is a top plan view of the jig and bone plate shown in FIG. 1.

FIGS. 1 and 2 are representative of jigs currently utilized. Referring generally to FIGS. 1 and 2, jig 12 may be provided to align cannulas (not shown) with respective fixation holes 16 on bone plate 10. Jig 12 may be attached to an end portion of plate 10 via fixation arm 20 so that, once plate 10 is positioned properly on a bone, cannulas may be passed through a plurality of holes 14 in jig 12 and advanced toward respective holes 16 in plate 10. Holes 14 in jig 12 are positioned and oriented to deliver fasteners to respective plate holes 16 in a desired trajectory. As best shown in FIG. 2, jig holes 14 may be laterally offset with respect to corresponding bone plate holes 16, so that respective axes of fasteners passed through the cannulas are directed toward the axis or center of the bone to which plate 10 is attached.

Jig 12 may be used with shorter bone plates by virtue of jig 12 being useable with plate 10, because the hole patterns of shorter bone plates relative to fixation arm 20 are contained within the hole pattern of plate 10. Referring again to FIG. 1, jig 12 may be used with shorter bone plates by using an appropriate number of jig holes 14 closest to fixation arm 20. Bone plate 10 has a generally straight or linear overall profile with fixation holes 16 that follow a consistent pattern across the body of plate 10, allowing the shorter bone plates to utilize the same jig holes 14 as the corresponding portion of bone plate 10. For example, when jig 12 is coupled with a short plate, only the jig holes 14 disposed between fixation arm 20 and short plate marker 22 are utilized. In bone plate 10, these jig holes 14 used with a short bone plate correspond with first set 30 of holes 16.

Similarly, jig holes 14 disposed between fixation arm 20 and middle marker 24 may be used for a medium length plate. These jig holes 14 correspond with both first set 30 and second set 32 of holes 16 in bone plate 10. For bone plate 10, jig holes 14 disposed between fixation arm 20 and long marker 26 (i.e., all of jig holes 14 on jig 12) may be used because bone plate 10 is a long length plate (as shown in FIGS. 1 and 2). These jig holes 14 correspond with first set 30, second set 32, and third set 34 of holes 16 in bone plate 10.

SUMMARY

The present disclosure provides a universal jig compatible with bone plates of varying size, in which different plate sizes having different hole configurations. For example, a longer bone plate may have a first hole pattern along a given length thereof, while various shorter bone plates may have differing hole patterns along respective corresponding lengths. The universal jig includes a combination of hole groupings to provide a jig hole for each hole in the differing hole patterns of the longer and shorter plates, so that the universal jig is useable with a variety of bone plates having disparate hole patterns. For any given bone plate length and hole configuration, a masking cover may be provided to attach to the jig. The masking cover masks off unused jig holes, so that only those jig holes intended for use with a particular bone plate are left exposed.

The universal jig may, for example, be used with periprosthetic ("PP") bone plates. PP bone plates include multiple fixation zones which allow the mounting of one portion of the plate to bone and another portion of the plate to a bone with a prosthesis mounted therein. Each fixation zone includes holes in a different geometrical arrangement. In a set of bone plates having differing lengths, any particular plate may include a non-periprosthetic zone ("non-PP zone") with a fixed length and hole configuration, and a periprosthetic zone ("PP zone") with a length and hole configuration that varies according to the length of the plate. The universal jig attaches to the PP bone plate proximate the PP zone, and includes jig holes corresponding to each bone plate hole in both the PP and non-PP zones for a variety of different plate lengths.

The invention, in one form thereof, comprises a bone plate fixation system including a first bone plate with a first bone plate body having a first bone plate longitudinal extent, the first bone plate body including a plurality of holes disposed along a portion of the first bone plate longitudinal extent and arranged in a first bone plate hole configuration. The bone plate fixation system further includes a second bone plate with a second bone plate body having a second bone plate longitudinal extent, the second bone plate body including a plurality of second bone plate holes disposed along a portion of the second bone plate longitudinal extent and arranged in a second bone plate hole configuration. The portion of the second bone plate longitudinal extent, along which the second bone plate holes are disposed, has a length approximately equal to the portion of the first bone plate longitudinal extent, along which the first bone plate holes are disposed. The second bone plate hole configuration is different from the first bone plate hole configuration. The bone plate fixation further includes a jig including a jig body having a jig body longitudinal extent, with the jig body having a plurality of cannula apertures. At least a portion of the plurality of cannula apertures are arranged along a portion of the jig body longitudinal extent to correspond to the first bone plate hole configuration, and at least a portion of the plurality of cannula apertures are arranged along the portion of the jig body longitudinal extent to correspond to the second bone plate hole configuration. The jig also includes a fixation arm extending from the jig body, the fixation arm attachable to the first bone plate and the second bone plate.

The invention, in another form thereof, comprises a bone plate fixation system including a first bone plate having a first bone plate set of holes, a jig, and a first masking cover. The jig includes a jig body with a plurality of cannula apertures, at least a portion of the plurality of cannula apertures positioned so that each hole of the first bone plate set of holes corresponds with a respective one of the plurality of cannula apertures. The jig also includes a fixation arm extending away from the jig body, the fixation arm adapted to attach the jig to the first bone plate. The bone plate fixation system further includes a first masking cover cooperating with the jig to expose each of the plurality of cannula apertures corresponding to the first bone plate set of holes, with the first masking cover covering each of the plurality of cannula apertures not corresponding to the first bone plate set of holes.

The invention, in a further form thereof, comprises a bone plate fixation system including a first bone plate with a first bone plate body having a first bone plate plurality of holes arranged in a first bone plate hole configuration. The bone plate fixation system also includes a jig with a jig body including a plurality of cannula apertures, at least a portion of the plurality of cannula apertures positioned so that each hole of the first bone plate plurality of holes corresponds with a respective one of the plurality of cannula apertures. The jig also includes a fixation arm extending away from the jig body, the fixation arm adapted to attach the jig to the first bone plate. The bone plate fixation system further includes means for identifying a subset of the plurality of cannula apertures corresponding to the first bone plate plurality of holes.

BRIEF DESCRIPTION OF THE DRAWINGS

The above mentioned and other features and advantages of the present disclosure, and the manner of attaining them, will become apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION

1. Universal Jig

Figure 3:
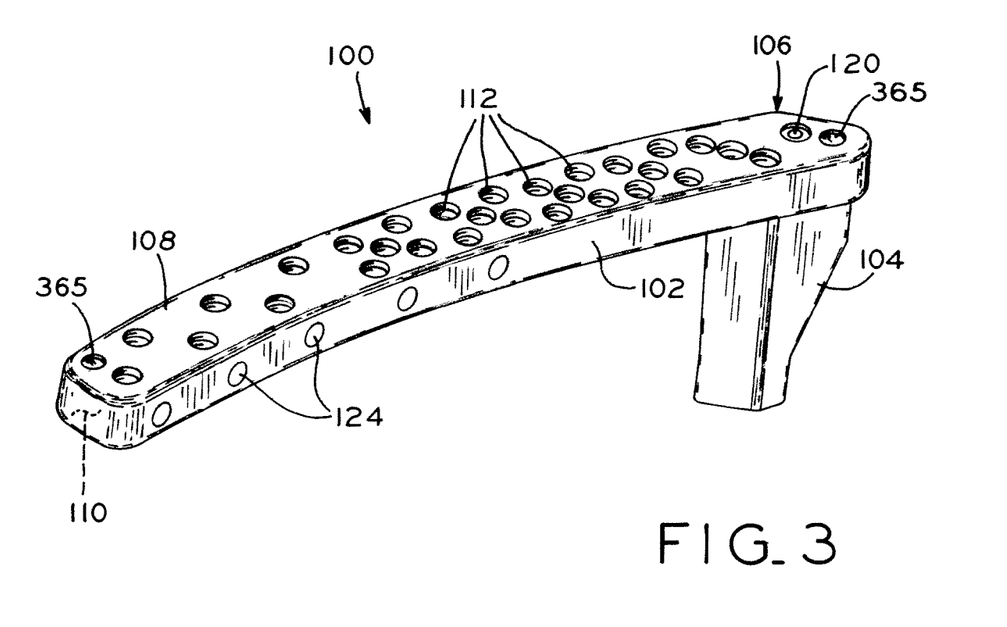
FIG. 3 is a universal jig in accordance with the present disclosure.

Referring to FIG. 3, universal jig 100 includes longitudinal body 102 with fixation arm 104 disposed at and extending away from head portion 106. Body 102 has upper face 108 and lower face 110, with a plurality of cannula apertures 112 extending therebetween. Cannula apertures 112 are arranged on body 102 so that each aperture 112 is distinct from another aperture 112, such that there is no overlap between the area of one aperture 112 and any other aperture 112. Jig 100 is useable with a variety of different periprosthetic ("PP") bone plates having varying hole patterns and lengths. For example, for multiple plates having differing hole patterns over a given length, universal jig 100 includes a combination of hole groupings to provide a jig hole for each hole in the differing hole patterns.

Figure 4:
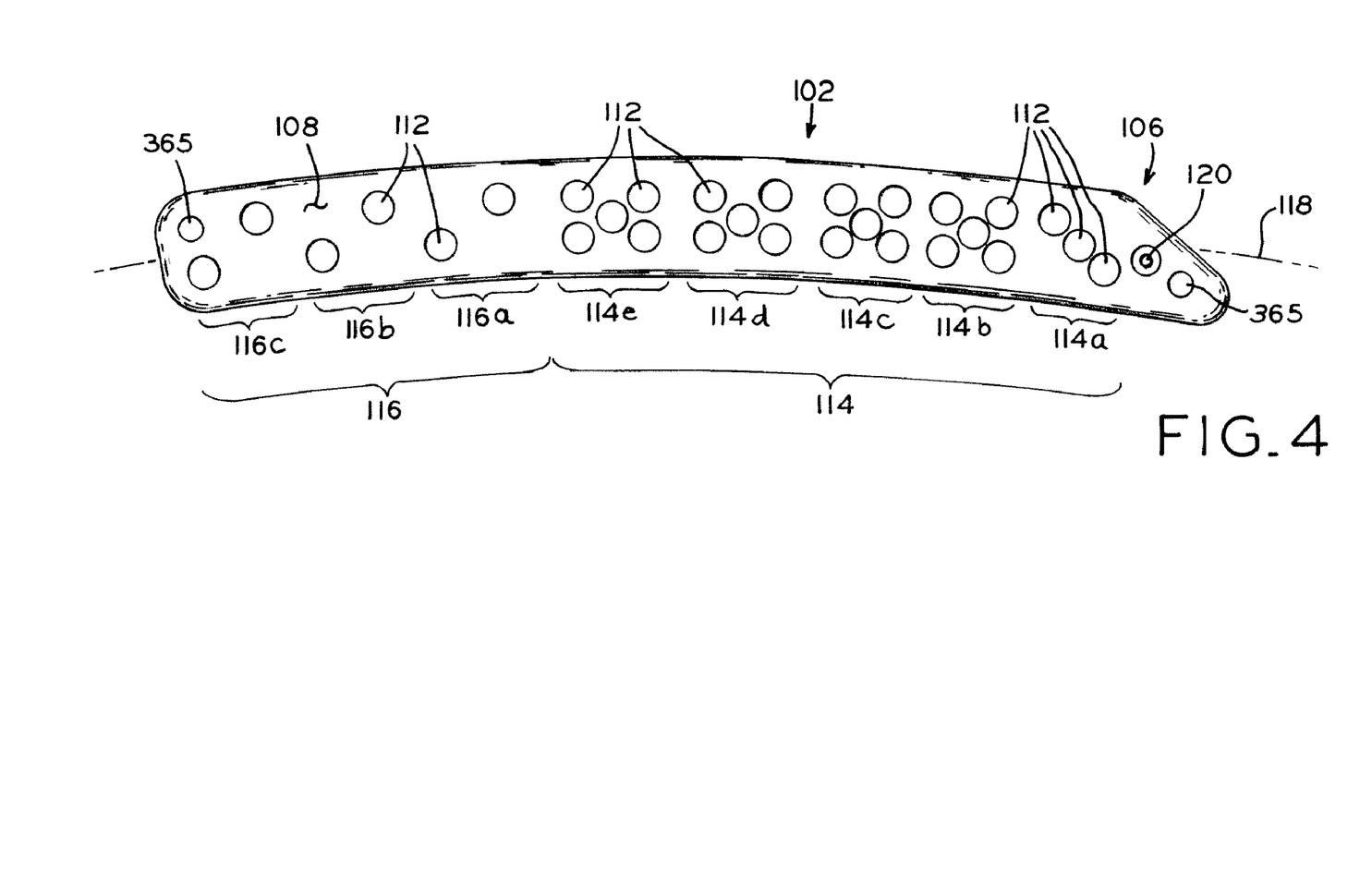
FIG. 4 is a top plan view of the universal jig shown in FIG. 3.

Referring now to FIG. 4, apertures 112 may be divided into first set 114 adapted to engage both periprosthetic holes ("PP holes") and non-periprosthetic holes ("non-PP holes") depending on plate length, and second set 116 adapted to engage only non-PP holes in a long plate length. As seen in FIGS. 12a-12e and described in more detail below, PP holes 207 are holes in a periprosthetic zone of a bone plate and are arranged in a pattern that facilitates engagement with a bone/prosthetic combination, while non-PP holes 203 are holes in a non-periprosthetic zone of a bone plate and are arranged in a pattern that facilitates engagement with a bone only. PP holes 207 and non-PP holes 203 combine to form a variable overall hole pattern on varying lengths of PP bone plates. Jig 100 is adapted to engage each of holes 203, as well as each of the holes 207 disposed between attachment area 212 (discussed in detail below) and holes 203, regardless of this variable overall pattern.

First set 114 of apertures 112 includes first grouping 114a having three apertures 112 arranged in a generally oblique orientation with respect to longitudinal axis 118 of body 102. Second, third, fourth and fifth groupings (114b, 114c, 114d and 114e, respectively) are arranged on body 102 so as to be increasingly distant from head portion 106. Groupings 114b, 114c, 114d, 114e each contain a diagonally arranged set of three apertures 112 similar to grouping 114a, and further include two additional apertures 112 flanking the middle hole of the three hole grouping to form an X-shaped pattern similar to the "five side" of a traditional six sided playing die.

Second set 116 of apertures 112 includes first grouping 116a, second grouping 116b and third grouping 116c, each including two diagonally arranged apertures 112, with first, second and third groupings 116a, 116b, 116c being increasingly distant from head portion 106 and from first set 114 of apertures 112. Groupings 116a, 116b, 116c have two apertures 112 arranged in a similar fashion to the additional holes added to first grouping 114a to create the five-hole groupings 114b-114e. As described in more detail below, these arrangements of hole groupings facilitate the use of universal jig 100 with a variety of bone plates having disparate hole patterns.

In the illustrated embodiment, universal jig 100 is adapted for use in conjunction with a bone plate to repair a fracture on a right-side bone, such as a right femur. However, a mirror image of jig 100 may be provided to similarly repair a left-side fracture. Moreover, the principles of operation of jig 100 disclosed herein are applicable to the affixation of a bone plate to any bone.

2. Periprosthetic Bone Plates Useable with the Universal Jig

Periprosthetic bone plates are used for repairing fractures in a bone having an existing or newly implanted prosthesis implanted in the bone. Referring to FIGS. 12a-12e, periprosthetic zones ("PP zone") 206, 226, 246, 266, 286 include PP holes 207 with a pattern adapted to engage a bone/prosthesis combination, while non-periprosthetic zones 202, 222, 242, 262, 282 include non-PP holes 203 adapted to engage a bone without a prosthesis. While a relatively smaller number of non-PP holes 203 may be used for a given length of fractured bone without a prosthesis, a relatively larger number of PP holes 207 may be used for the same length of bone with a prosthesis implanted therein. Thus, different lengths of a PP bone plates typically have different overall hole patterns.

Universal jig 100 may be used with PP bone plates including PP zones and non-PP zones, where each zone has a different hole pattern. In the illustrated embodiments, universal jig 100 is adapted to engage five different lengths of PP bone plates, although it is contemplated that the present disclosure may be adapted to engage fewer or more sizes of bone plates as required or desired. Exemplary PP bone plates are shown and described in a U.S. patent application entitled A PLATE FOR THE TREATMENT OF BONE FRACTURES (Attorney Docket No. ZIM0793), filed on even date herewith, which claims priority from European Patent Application No. EP09008867.5 filed Jul. 7, 2009, the disclosures of which are hereby expressly incorporated by reference herein in their entireties.

A variety of plate sizes are shown in FIGS. 12a-12e. Short size plate 200, best seen in FIGS. 5 and 12a, includes non-PP zone 202, transition zone 204 and PP zone 206. Non-PP zone 202 includes six non-PP holes 203. PP zone 206 includes ten PP holes 207 (FIG. 12a), as well as jig registration holes 214 and jig fixation hole 216 (described below). Each of holes 203, 207 extends between bone contacting surface 217 and fixation surface 218. PP zone 206 terminates at head portion 208 of plate 200, and tail portion 210 terminates at non-PP zone 202 of plate 200. Attachment area 212 is used for the attachment of universal jig 100 to plate 200, as described herein.

Figures 12A, 12B, 12C:
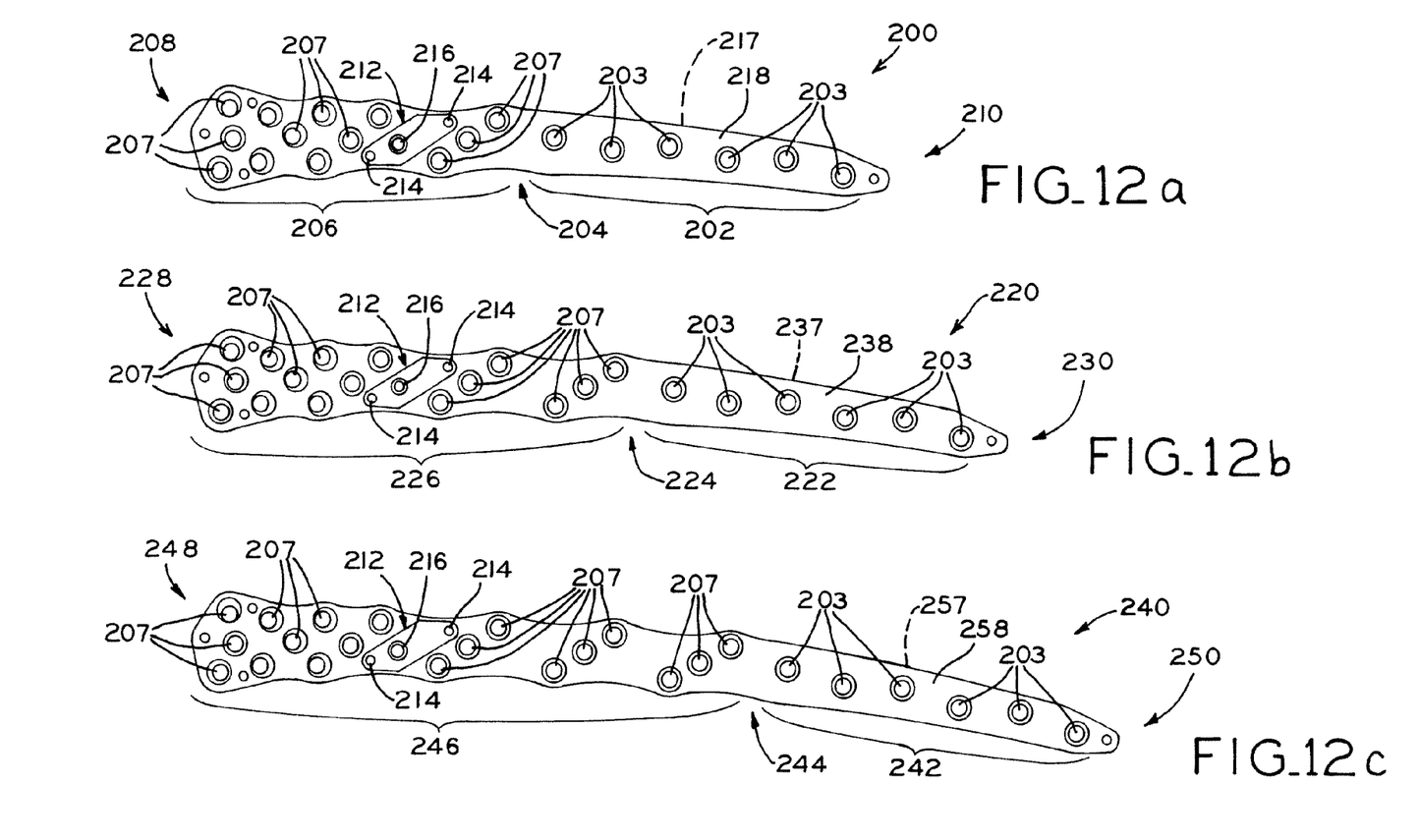
FIGS. 12(a)-12(e) are top plan views of PP bone plates, illustrating short, medium-short, medium, medium-long and long plates respectively.

Medium-short size plate 220 similarly includes non-PP zone 222, transition zone 224 and PP zone 226. Medium-short plate 220 is similar to short plate 200, except that PP zone 226 includes three additional PP holes (i.e., one additional set of three holes) 207 extending between bone contacting surface 237 and fixation surface 238, as compared to short plate 200. Accordingly, non-PP zone 222 is located further from head portion 228 of plate 200. However, attachment area 212 remains in the same position on plate 220 with respect to head portion 228 as attachment area 212 on plate 200. Plate 220 is therefore longer than plate 200, increasing the distance between non-PP zone 222 and attachment area 212.

Medium size plate 240 similarly includes non-PP zone 242, transition zone 244 and PP zone 246. PP zone 246 includes three additional PP holes (i.e., one additional set of three holes) 207 extending between bone contacting surface 257 and fixation surface 258, as compared with medium-short plate 220. Again, attachment area 212 remains in the same position on plate 240 with respect to head portion 248 as attachment area 212 on plates 200 and 220. Plate 240 is therefore longer than plate 220 and further distancing non-PP zone 242 from attachment area 212.

Figures 12D, 12E:
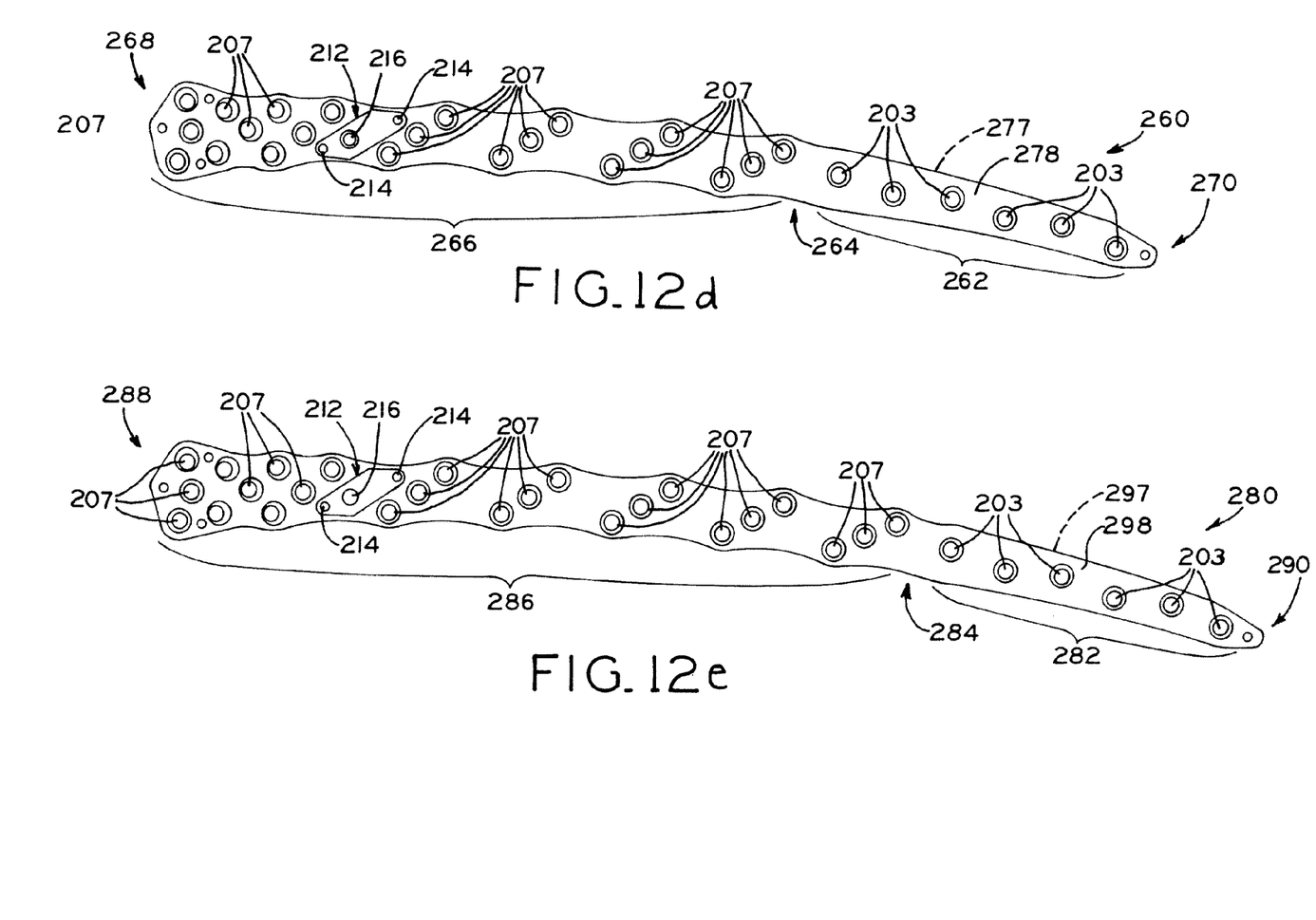

Medium-long plate 260 similarly includes non-PP zone 262, transition zone 264 and PP zone 266. PP zone 266 includes three additional PP holes 207 extending between bone contacting surface 277 and fixation surface 278, as compared with plate 240. Again, attachment area 212 remains in the same position on plate 260 with respect to head portion 268 as attachment area 212 on plates 200, 220 and 240. Plate 260 is therefore longer than plate 240, and non-PP zone 262 is still further distanced from head portion 268 as compared with head portion 248 and non-PP zone 242 of plate 240.

Long plate 280 includes non-PP zone 282, transition zone 284 and PP zone 286. PP zone 286 includes yet another three additional PP holes 207 extending between bone contacting surface 297 and fixation surface 298, as compared with plate 260. Attachment area 212 again remains in the same position on plate 280 with respect to head portion 288 as attachment area 212 on plates 200, 220, 240 and 260. Plate 280 is therefore the longest of the five plates illustrated in FIGS. 12a-12e, and non-PP zone 282 is still further distanced from head portion 288 as compared with head portion 268 and non-PP zone 262 of plate 260.

Moreover, for all of plates 200, 220, 240, 260 and 280, attachment area 212 remains in the same spatial location with respect to respective head portions 208, 228, 248, 268, 288 of each plate. A relatively longer PP plate has three additional PP holes 207 disposed between attachment area 212 and the respective transition zones 204, 224, 244, 264, 284, as compared with the next shorter-size plate. As described in more detail below, the consistent positioning of attachment area 212 with respect to head portions 208, 228, 248, 268, 288 facilitates use of various PP plates in an MIS procedure, but also results in a varying spatial relationship of respective non-PP zones 202, 222, 242, 262, 282 with respect to attachment area 212. Despite this variance, universal jig 100 is suitable for use with all of plates 200, 220, 240, 260, 280.

3. Masking Covers

Figure 5:
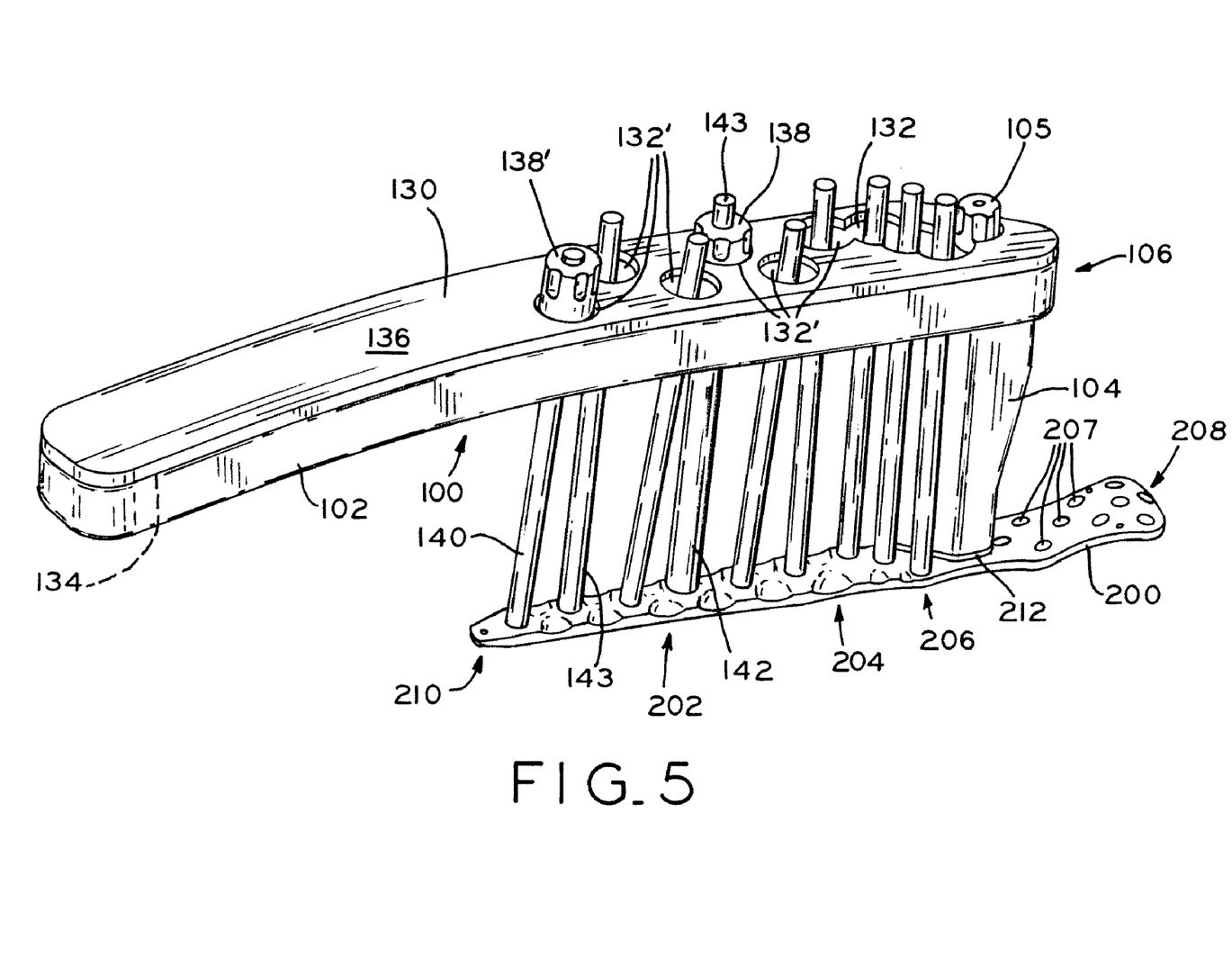
FIG. 5 is a perspective view of the universal jig shown in FIG. 3 attached to a PP bone plate and having a masking cover used in cooperation with a short size PP bone plate secured thereto.

In the illustrated embodiments, no single bone plate utilizes all of apertures 112 in body 102 of universal jig 100. Referring generally to FIGS. 5-10, one or more masking covers may be provided to mask off unused cannula apertures 112 for a given length and configuration of bone plate. For example, as shown in FIG. 5, masking cover 130 may be provided for use with short plate 200 to mask or cover unused cannula apertures 112 while leaving exposed cannula apertures 112 corresponding to respective holes in non-PP zone 202 and PP zone 206 on plate 200. More particularly, and as shown in FIG. 7, masking cover 130 includes a plurality of apertures 132, 132' extending from lower surface 134 to upper surface 136 of masking cover 130, with apertures 132, 132' positioned to provide access to only those cannula apertures 112 used with short plate 200.

Referring to FIGS. 5-7 and 12a, masking cover 130 includes first set of holes 148 (FIGS. 6 and 7) comprised of apertures 132', which are positioned to make accessible those cannula apertures 112 in body 102 of jig 100 which correspond to non-PP holes 203 in non-PP zone 202 of short plate 200 (FIG. 12a). Masking cover 130 further includes second set of holes 149 (FIGS. 6 and 7) comprised of apertures 132 adapted to make accessible those cannula apertures 112 which correspond with PP holes 207 in the portion of PP zone 206 between attachment area 212 and transition zone 204 of short plate 200 (FIG. 12a). Apertures 132, 132' are oversized as compared to cannula apertures 112 to accommodate head portion 138' of stabilization bolt 140 and/or knurled portion 138 of protection sleeve 142 (FIGS. 5 and 6) as described in detail below.

Referring now to FIG. 7, masking cover 130 may further include registration pins 144 which are sized and positioned to engage unused cannula apertures 112 to establish and maintain proper positioning of masking cover 130 on body 102 of jig 100. Registration pins 144 may alternatively be sized and positioned to engage dedicated registration holes 365 (as shown in FIG. 3). When masking cover 130 is placed on body 102 of jig 100, registration pins 144 fit in to corresponding holes on body 102 to locate masking cover 130. If masking cover 130 is not properly positioned on body 102, pins 144 will not both fit into corresponding holes on body 102, thereby providing an indication to the user that masking cover 130 needs to be repositioned. The holes corresponding to pins 144 are unused ones of cannula holes 112. Optionally, masking cover 130 may also include a marking or engraving 146 along a perimeter edge of cover 130 to identify a particular bone plate associated with masking cover 130, such as short plate 200, and whether cover 130 is intended for use on a right or left side anatomical structure. In the illustrated embodiment of FIG. 7, for example, marking 146 indicates that plate 130 is designed for use with a right-side jig and a 240 mm bone plate at a distal end of a bone (such as, for example, a femur).

Turning now to FIGS. 8-10 and 12e, masking cover 150 may be provided for use with universal jig 100 and long plate 280. Masking cover 150 is similar to masking cover 130, in that it has a plurality of apertures 152, 152' extending between lower surface 154 and upper surface 156 of cover 150. However, apertures 152, 152' of masking cover 150 vary in configuration and number as compared with apertures 132, 132' of masking cover 130. Apertures 152, 152' are, similar to apertures 132, 132', sized to allow knurled portions 138, and/or head portion 138' to pass therethrough.

Masking cover 150 includes first set of holes 168 comprising apertures 152' (FIGS. 9 and 10) adapted to make accessible those cannula apertures 112 in body 102 of jig 100 which correspond to non-PP holes 203 in non-PP zone 282 of long plate 280 (FIG. 12e). Masking cover 150 further includes second set of holes 169 comprising apertures 152 (FIGS. 9 and 10) adapted to make accessible those cannula apertures 112 which correspond with PP holes 207 in the portion of PP zone 286 between attachment area 212 and transition zone 284 of long plate 280 (FIG. 12e).

Similar to masking cover 130, masking cover 150 may also include a marking or engraving 166 identifying the corresponding bone plate, such as long plate 280, by length and/or anatomical side. In the illustrated embodiment of FIG. 10, for example, marking 166 indicates that plate 150 is designed for use with a right-side jig and a 400 mm bone plate at a distal end of a bone, such as a femur. At least one registration pin 164 (FIG. 10) may also be included in at least one location on lower surface 154 of masking cover 150 to facilitate positioning and retention of masking cover 150 on body 102 of jig 100, similar to registration pin 144 of cover 130 (discussed above).

Figure 11:
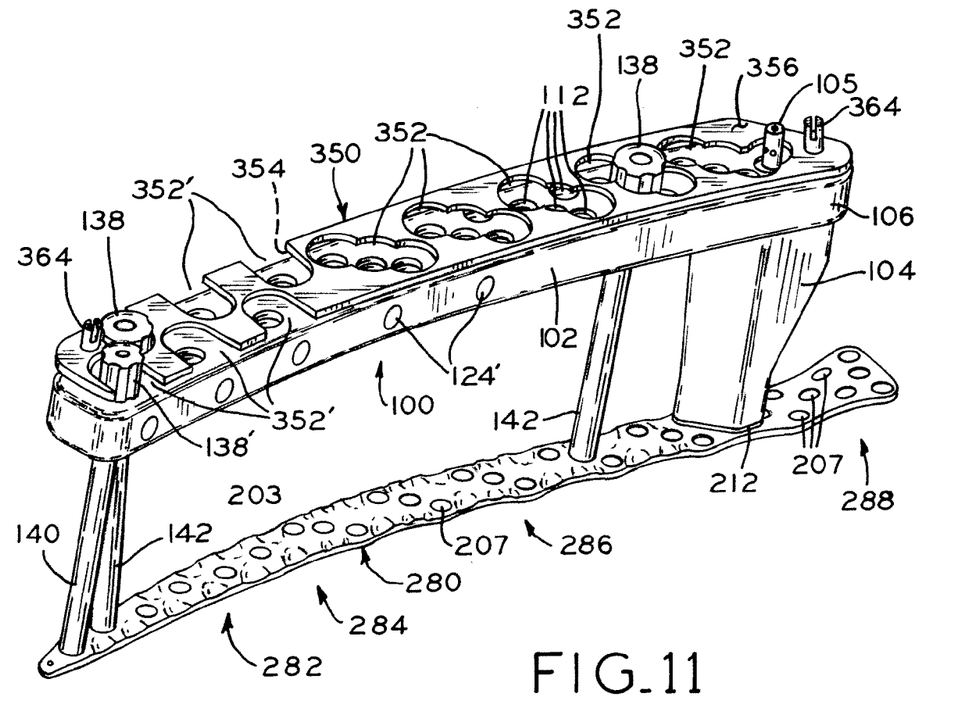
FIG. 11 is a perspective view of the universal jig shown in FIG. 3, illustrating an alternative masking cover used in cooperation with a long size bone plate.

Referring now to FIG. 11, an alternative masking cover 350 is shown. Masking cover 350 includes apertures 352, and cutouts 352' extending from lower surface 354 to upper surface 356. Apertures 352 correspond to PP holes 207 of plate 280, which are similar to apertures 132, 152 of covers 130, 150. However, cutouts 352' correspond to non-PP holes 203 of plate 280, rather than apertures 132', 152' of covers 130, 150. Cutouts 352' are suitable for use with thin masking cover materials because potentially delicate strips of material separating cutouts 352' from a perimeter edge of cover 350 are not included.

Masking cover 350 includes registration pins 364 at each end of cover 350. Similar to registration pins 144, 164 of covers 130, 150 respectively, pins 364 cooperate with registration holes 365 in body 102 (FIGS. 3 and 4) to orient and secure cover 350 to body 102, and to prevent the misalignment of cover 350 on body 102. Unlike pins 144, 164, pins 364 extend from both lower surface 354 and upper surface 356, so that cover 350 is securable to both a right-side jig (such as shown in FIG. 11) or a left-side jig (which is a mirror image of right-side jig 100, as discussed above) by flipping cover 350 over. Pins 364 may replace registration pins 144, 164 of covers 130, 150 respectively, or may be used in addition to such registration pins.

Figure 10:
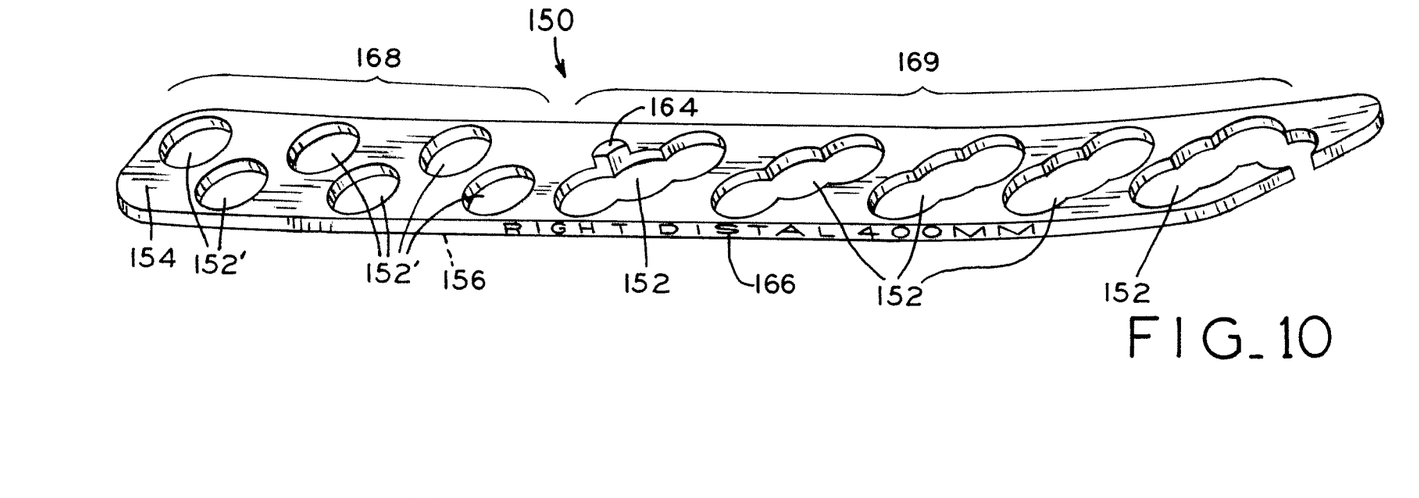
FIG. 10 is a perspective view of the masking cover illustrated in FIG. 8, shown without the bone plate and jig.

Covers 130, 150 and 350 have been described for short plate 200 and long plate 280. However, the principles of operation for covers 130, 150, 350 also apply in combination with one another, and for use with other lengths and orientations of bone plates. For example, masking covers may be provided for medium-short plate 220, medium plate 240, medium-long plate 260, or other periprosthetic bone plates by providing an appropriate number and orientation of respective apertures to correspond with any respective plate. Registration pins 144, 164, 364 may also extend from only one side of their respective masking covers to correspond with either a left-side or right-side jig (as shown in FIGS. 7 and 10 with respect to pins 144, 164), or registration pins 144, 164, 364 may extend from both sides of their respective masking covers to facilitate use of a single cover for both right-side and left-side jigs (as shown in FIG. 11 with respect to pins 364).

4. Use of the Universal Jig System

Figure 7:
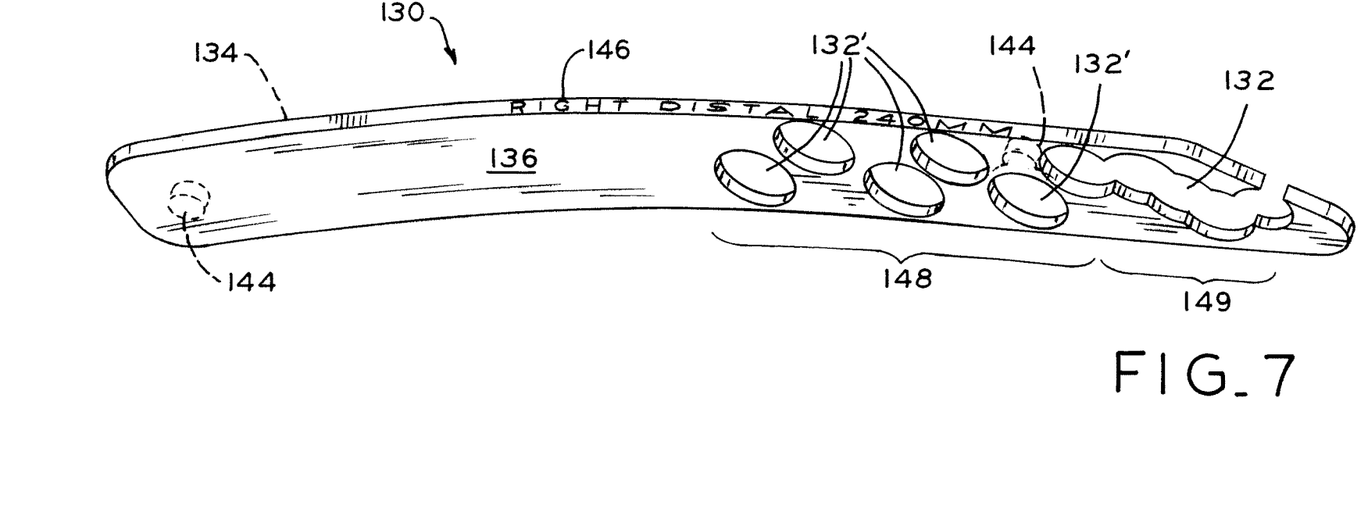
FIG. 7 is a perspective view of the masking cover illustrated in FIG. 5, shown without the bone plate and jig.
Figures 8, 9:
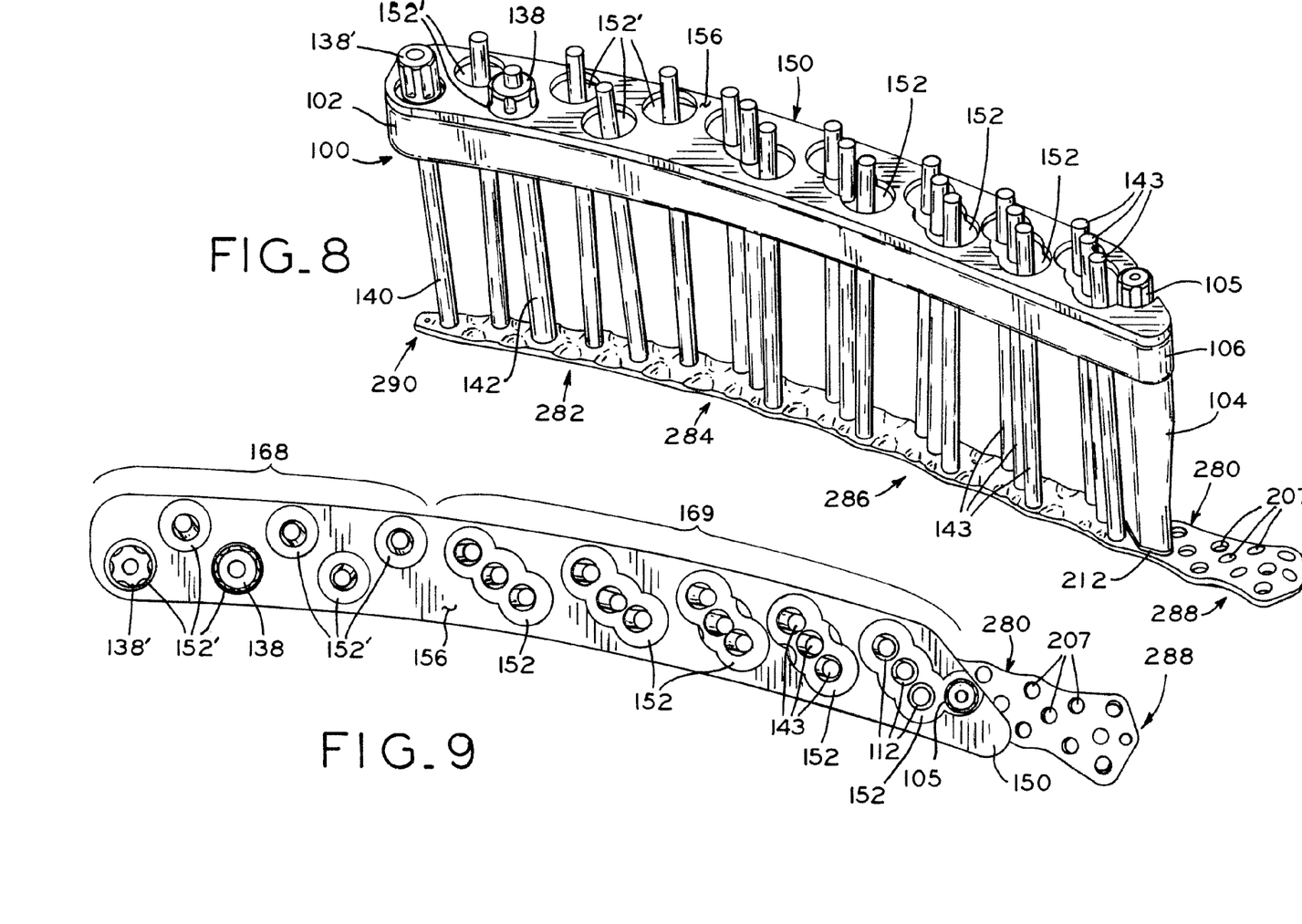
FIG. 8 is a perspective view of the universal jig shown in FIG. 3, illustrating a masking cover used in cooperation with a long size PP bone plate.
FIG. 9 is a top plan view of the universal jig, bone plate and masking cover shown in FIG. 8.

In use, universal jig 100 allows for the percutaneous implantation of fasteners to fasten various sizes of periprosthetic bone plates to a bone, thereby allowing for smaller incisions consistent with goals of MIS techniques. By way of illustration, the use of jig 100 will be described with respect to short plate 200, as shown in FIGS. 5-7 and 12a. Similar methodology is used for other bone plates of different lengths, such as with long plate 280 as shown in FIGS. 8 and 9. Jig 100 may also be used in conjunction with PP bone plates for a variety of anatomical structures, and in proximal or distal fractures. By providing a right-side jig (such as jig 100) and left-side jig (a mirror image of jig 100, as discussed above), a universal jig in accordance with the present disclosure is also useable in both left- and right-side applications.

Figure 6:
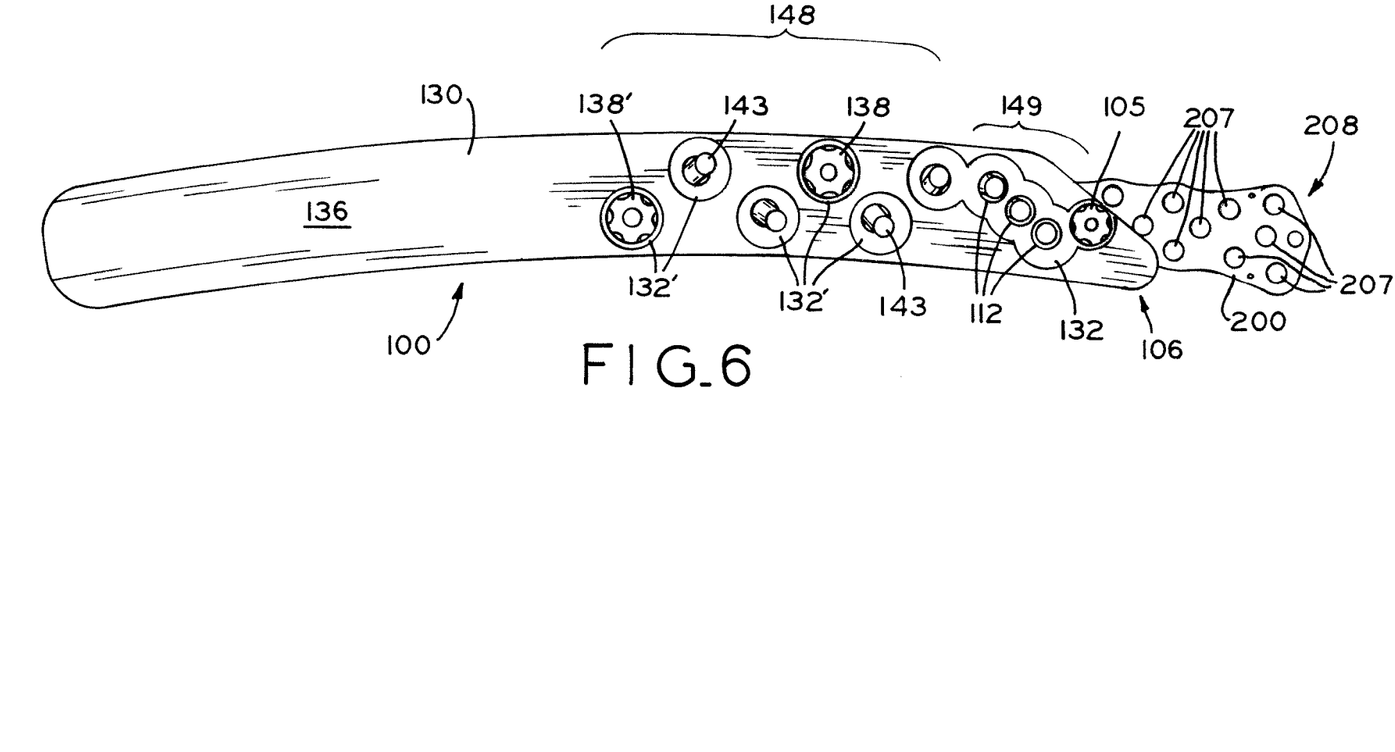
FIG. 6 is a top plan view of the universal jig, bone plate and masking cover shown in FIG. 5.

Jig 100 may be used with short sized PP bone plate 200 as shown in FIGS. 5 and 6. Fixation arm 104 of jig 100 is first attached to short size bone plate 200 at attachment area 212 (FIG. 12a). To facilitate and maintain an accurate orientation of jig relative to bone plate 200, fixation arm 104 includes two jig registration pins (not shown) sized and positioned to correspond with orientation holes 214 in attachment area 212. Attachment aperture 120 (FIGS. 3 and 4) is provided in head portion 106 of body 102 and extends through fixation arm 104 to provide a path for arm fastener 105 (FIGS. 5 and 6) to pass through body 102 and fixation arm 104 and to engage threaded fixation hole 216 in attachment area 212 of plate 200.

With jig 100 attached to plate 200 via fixation arm 104, a small incision is made near an end of a fractured bone. Plate 200 is then inserted through the incision, leading with tail portion 210, and into contact the fractured bone. When plate 200 is inserted so that head portion 208 is near the end of the fractured bone and with plate 200 spanning the fracture, jig 100 is used to attach plate 200 to the fractured bone. More particularly, stabilization bolt 140 is used to secure tail portion 210 of plate 200 to jig 100, as well as to ensure proper spacing between jig 100 and bone plate 200. Stabilization bolt 140 also provides a path for passage of a fastening element to attach tail portion 210 to a bone, as described below.

An appropriate aperture 112 is selected for threaded attachment of stabilization bolt 140 (FIG. 5) to jig 100 at the non-PP hole 203 closest to the end of tail portion 210 of plate 200. Masking cover 130 may optionally be utilized to mask off unused apertures 112 for short size plate 200, as described in detail above, in which case the aperture 132' farthest from head portion 106 corresponds to hole 203 for use with stabilization bolt 140. However, appropriate ones of apertures 112 corresponding with holes 203, 207 may also be selected without masking cover 130.

With the proper aperture 112 selected for use with stabilization bolt 140, a stab incision is made through the selected cannula aperture 112. Stabilization bolt 140 is advanced through the incision and threaded into non-PP hole 203 to secure jig 100 to tail portion 210 of plate 200 (FIG. 5). Once threaded into hole 203, body 102 of jig 100 may be adjusted along the axis of bolt 140 to bring head portion 138' of stabilization bolt 140 into contact with upper face 108 of body 102. While maintaining such contact, a lock pin (not shown) is inserted into body 102 to ensure the proper distance is maintained.

Referring now to FIG. 3, transverse holes 124 are provided in jig 100 to facilitate securement of stabilization bolt 140 to body 102. Stabilization bolt 140 includes a groove (not shown) which intersects with one of transverse holes 124 when bolt 140 is received within cannula aperture 112. A lock pin (not shown) may be passed into a respective transverse hole 124 to engage the groove on stabilization bolt 140, thereby securing stabilization bolt 140 to body 102 of jig 100. As shown in FIG. 3, five transverse holes 124 are provided in body 102 to correspond with the position of stabilization bolt 140 for each of the five lengths of bone plates 200, 220, 240, 260, 280.

Referring generally to FIG. 5, head portion 208 is then secured to the bone via PP holes 206 using any suitable methods and fasteners (not shown). With head portion 208 secured, a wire (not shown) inserted through stabilization bolt 140 may be used to secure tail portion 210 of plate 200 to the fractured bone. A second stab incision is then made through a chosen one of the remaining available cannula apertures 112 in body 102. Protection sleeve 142 is then inserted through the chosen aperture 112 so that it extends into the second stab incision at the proper location and with the proper trajectory toward the corresponding hole 203 or 207 in plate 200. Protection sleeve 142 may include a drill guide 143 received therein, which is then threaded into the threaded hole of the bone plate. A trocar (not shown) may also be included to aid in passage of protection sleeve 142 through the second stab incision.

With protection sleeve 142 proximate plate 200 and a respective one of holes 203, 207, protection sleeve 142 is screwed into cannula aperture 112 of body 102 of jig 100 so that protection sleeve 142 comes into contact with plate 200. Drill guide 143 may then be used to drill a pilot hole for a fastener, and may subsequently be removed from protection sleeve 142 to allow a fastener to be passed therethrough and to fasten plate 200 to the bone. This procedure may be repeated in other cannula apertures 112 of jig 100 as desired or required for a particular surgical procedure, until plate 200 is satisfactorily secured to the bone. Any remaining protection sleeves 143 may then be removed. Universal jig 100 may then be disconnected from plate 200 by removing stabilization bolt 140 and fixation arm fastener 105 from body 102 and fixation arm 104, respectively.

Cannula apertures 112 of jig 100 correspond to both PP holes 207 and non-PP holes 203 in PP zone 206 and non-PP zone 202, respectively. Thus, jig 100 may be used to secure plate 200 to a part of a bone with no existing prosthesis by using selected cannula apertures 112 corresponding with non-PP zone 202, and may also be used to secure plate 200 to a part of a bone with an existing prosthesis implanted in the bone by using selected cannula apertures 112 corresponding with PP zone 206.

Advantageously, universal jig 100 may be used with a variety of PP plates having different lengths, such as PP plates 200, 220, 240, 260, 280 as shown in FIGS. 12a-12e, respectively. The multiple holes found in first set of holes 114 and second set of holes 116 in body 102 allow universal jig 100 to engage both non-PP holes 203 and PP holes 207 in any of a variety of plate lengths, while still allowing fixation arm 104 of jig 100 to attach to an attachment area 212 so that head portion 208 of each plate has a consistent spatial relationship with universal jig 100 regardless of plate length. Put another way, universal jig 100 obviates the need for separate jigs for each plate length, despite variation in the distance between attachment area 212 and non-PP zones 202, 222, 242, 262, 282 in each plate.

Further, the configuration of body 102 of universal jig 100 allows cannula apertures 112 to be distinct one from the other, thereby preventing any overlap of the areas of cannula apertures 112. Advantageously, preventing such overlap maintains material contact between body 102 and stabilization bolt 140 and/or protection sleeves 142, thereby ensuring a rigid and accurate connection therebetween for all cannula apertures 112. However, cannula apertures 112 may be considered to be "distinct" within the scope of the present disclosure even where there is some amount of "overlap" between neighboring cannula apertures 112, provided the overlapping cannula apertures 112 adequately secure and orient protection sleeves 142 (or another structure contained by a cannula aperture 112).

The optional inclusion of masking covers 130, 150 or 350 as well as similarly constructed masking covers for intermediate plate sizes, promotes ease of use of universal jig 100 by exposing only cannula apertures 112 which are used for a particular plate. By providing these masking covers, universal jig 100 retains the advantage of being useable with multiple plate sizes, while allowing access to only those cannula apertures which would be present in a jig made specifically for a given plate size.

Still further, universal jig 100 may be used with bone plates having a variety of head portion geometries. Although a particular geometry of head portion 208 is shown in the illustrated embodiments, the head portion of any length of PP bone plate may be altered without affecting the usability of jig 100. Stated another way, because jig 100 attaches to attachment area 212 via fixation arm 104, the portion of plate 200, 220, 240, 260, 280 between attachment area 212 and head portion 208 may be altered as required or desired for a particular application without affecting the interaction between jig 100 and plate 200, 220, 240, 260, 280.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A bone plate fixation system comprising:
   a first bone plate comprising a first bone plate body having a first bone plate longitudinal extent, said first bone plate body including a plurality of first bone plate holes disposed along a portion of said first bone plate longitudinal extent and arranged in a first bone plate hole configuration;
   a second bone plate comprising a second bone plate body having a second bone plate longitudinal extent, said second bone plate body including a plurality of second bone plate holes disposed along a portion of said second bone plate longitudinal extent and arranged in a second bone plate hole configuration, said portion of said second bone plate longitudinal extent along which said second bone plate holes are disposed having a length approximately equal to said portion of said first bone plate longitudinal extent along which said first bone plate holes are disposed, said second bone plate hole configuration different from said first bone plate hole configuration;
   a jig comprising:
   a jig body having a jig body longitudinal extent, said jig body including a plurality of cannula apertures, at least a portion of said plurality of cannula apertures arranged along a portion of said jig body longitudinal extent to correspond to said first bone plate hole configuration, at least a portion of said plurality of cannula apertures arranged along said portion of said jig body longitudinal extent to correspond to said second bone plate hole configuration,
   wherein said first bone plate hole configuration and said second bone plate hole configuration are each arranged along a common length of said jig body; and
   a fixation arm extending from said jig body, said fixation arm attachable to said first bone plate and said second bone plate; and
   a first masking cover adapted to mount to said jig and cooperate with said first bone plate, said first masking cover comprising:
   a first masking cover upper surface and a first masking cover lower surface; and
   a plurality of first masking cover apertures extending between said first masking cover upper surface and said first masking cover lower surface, said first masking cover apertures positioned to identify a subset of said plurality of cannula apertures corresponding to said plurality of first bone plate holes.

2. The bone plate fixation system of claim 1, wherein said first bone plate hole configuration and said second bone plate hole configuration each comprise a periprosthetic zone and a non-periprosthetic zone.

3. The bone plate fixation system of claim 1, wherein said first masking cover further comprises at least one first masking cover registration pin adapted to cooperate with said jig, said first masking cover registration pin operable to restrain movement of said first masking cover relative to said jig when said first masking cover is mounted to said jig.

4. The bone plate fixation system of claim 1, further comprising:
   a second masking cover adapted to mount to said jig and cooperate with said second bone plate, said second masking cover comprising:
   a second masking cover upper surface and a second masking cover lower surface; and
   a plurality of second masking cover apertures extending between said second masking cover upper surface and said second masking cover lower surface, said second masking cover apertures positioned to identify a subset of said plurality of cannula apertures corresponding to said plurality of second bone plate holes.

5. The bone plate fixation system of claim 4, wherein said second masking cover further comprises at least one second masking cover registration pin adapted to cooperate with said jig, said second masking cover registration pin operable to restrain movement of said second masking cover with respect to said jig when said second masking cover is mounted to said jig.

6. The bone plate fixation system of claim 1, wherein at least a portion of said plurality of said cannula apertures in said jig has both a corresponding first bone plate hole in said first bone plate and a corresponding second bone plate hole in said second bone plate.

7. The bone plate fixation system of claim 1, wherein the number of second bone plate holes in said second bone plate exceeds the number of first bone plate holes in said first bone plate.

* * * * *